United States Patent
Bjaerum et al.

(10) Patent No.: US 6,592,522 B2
(45) Date of Patent: Jul. 15, 2003

(54) ULTRASOUND DISPLAY OF DISPLACEMENT

(75) Inventors: Steinar Bjaerum, Horten (NO); Bjorn Olstad, Stathelle (NO); Kjell Kristoffersen, Oslo (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,084

(22) Filed: Jun. 10, 2002

(65) Prior Publication Data

US 2003/0013963 A1 Jan. 16, 2003

Related U.S. Application Data

(60) Provisional application No. 60/297,572, filed on Jun. 12, 2001.

(51) Int. Cl.$^7$ .................................................. A61B 8/00
(52) U.S. Cl. .................... 600/443; 600/443; 600/437; 600/444; 600/453; 600/455; 600/454; 600/456
(58) Field of Search ................................. 600/443, 437, 600/444, 455, 453, 454, 456

(56) References Cited

U.S. PATENT DOCUMENTS

| | | | |
|---|---|---|---|
| 5,628,321 A | 5/1997 | Scheib et al. | |
| 5,820,561 A | 10/1998 | Olstad et al. | |
| 5,846,202 A | 12/1998 | Ramamurthy et al. | |
| 5,910,119 A | 6/1999 | Lin | |
| 5,921,931 A | * 7/1999 | O'Donnell et al. | 600/441 |
| 6,110,119 A | * 8/2000 | Hall | 600/455 |
| 6,126,605 A | * 10/2000 | Washburn et al. | 600/454 |

* cited by examiner

Primary Examiner—Marvin M. Lateef
Assistant Examiner—Maulin Patel
(74) Attorney, Agent, or Firm—McAndrews, Held & Malloy, Ltd.; Peter J. Vogel; Michael A. Dellapenna

(57) ABSTRACT

An ultrasound machine that generates a color representation of moving structure, such as cardiac wall tissue within a region of interest, and is displayed on a monitor. The color representation is generated by displaying at least one color characteristic related to a set of signal values of the structure, such as velocity or strain rate. The related feature of the set of signal values is mapped to the color characteristic by an apparatus comprising a front-end that generates received signals in response to backscattered ultrasound waves. A Doppler processor generates a set of signal values representing a spatial set of values of the moving structure. A host processor embodies a tracking function and a time integration function to generate tracked movement parameter profiles and displacement parameter values over a time period corresponding to sampled anatomical locations within the region of interest. The displacement parameter values are then mapped to color characteristic signals. A display processor maps the values of the color characteristic signals to the displacement parameter values, representing the moving structure, to display a color representation, on a monitor.

20 Claims, 9 Drawing Sheets

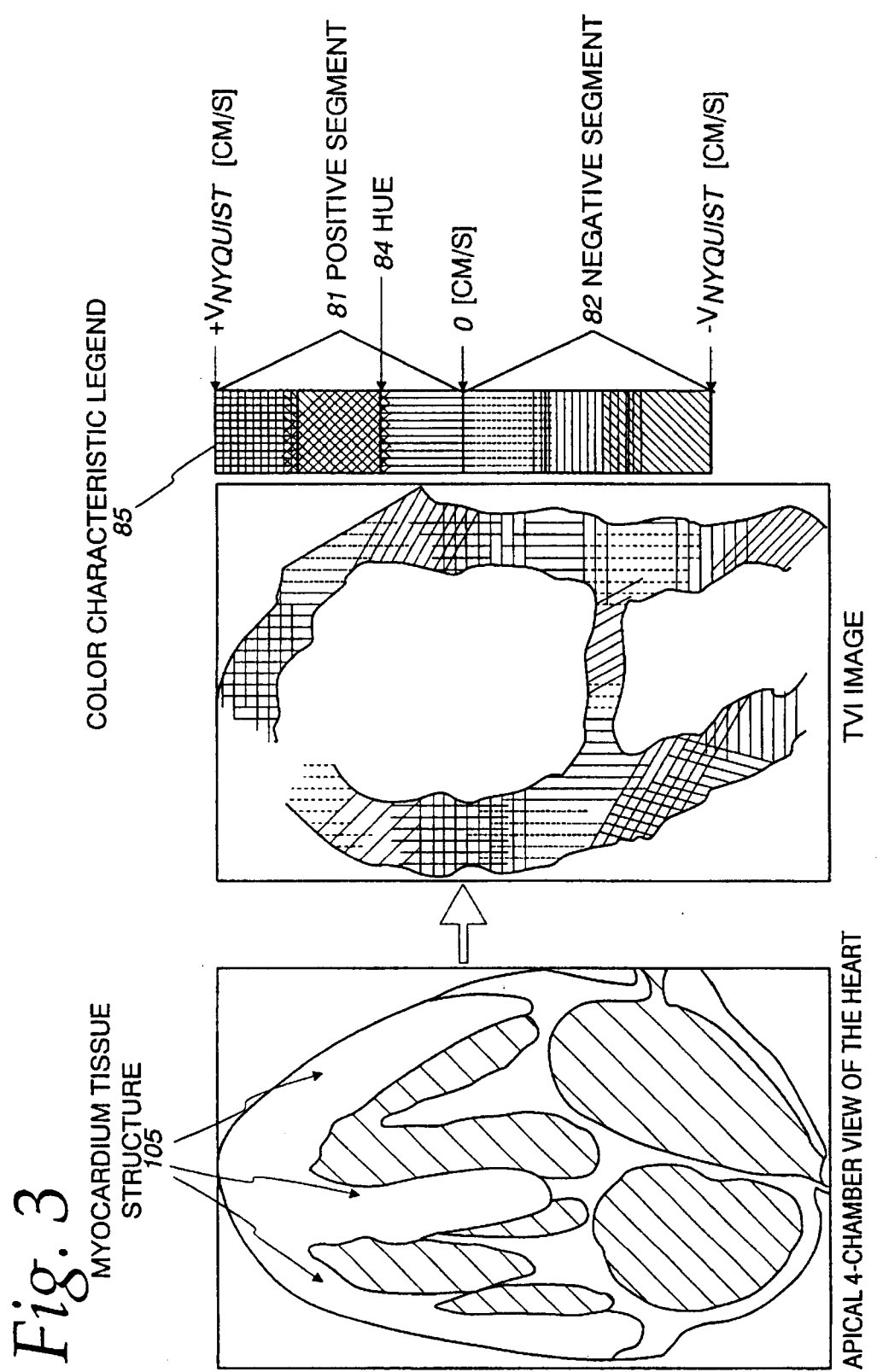

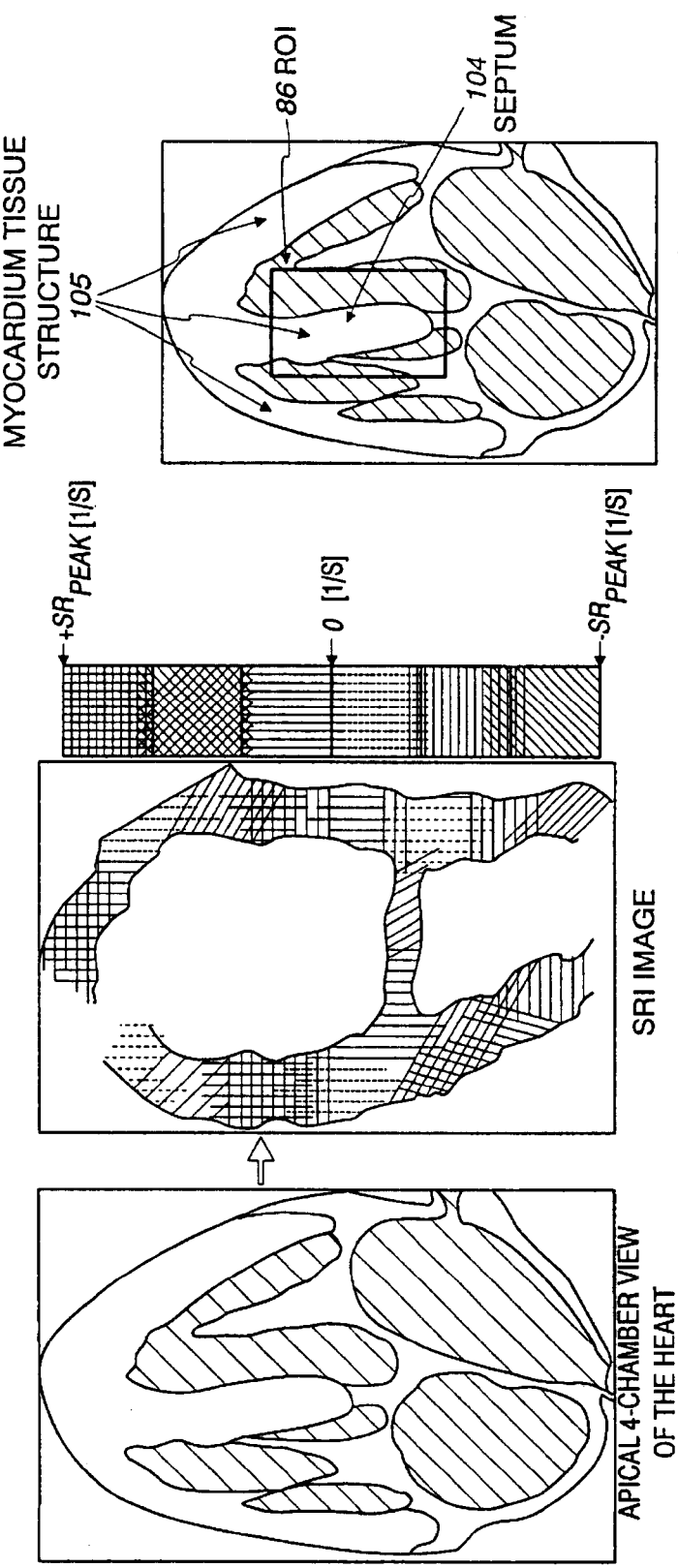
Fig. 6 MYOCARDIUM TISSUE STRUCTURE
86 ROI
104 SEPTUM
105
APICAL 4-CHAMBER VIEW OF HEART
SRI IMAGE
Fig. 4 APICAL 4-CHAMBER VIEW OF THE HEART
Fig. 5
47 ECG SIGNAL

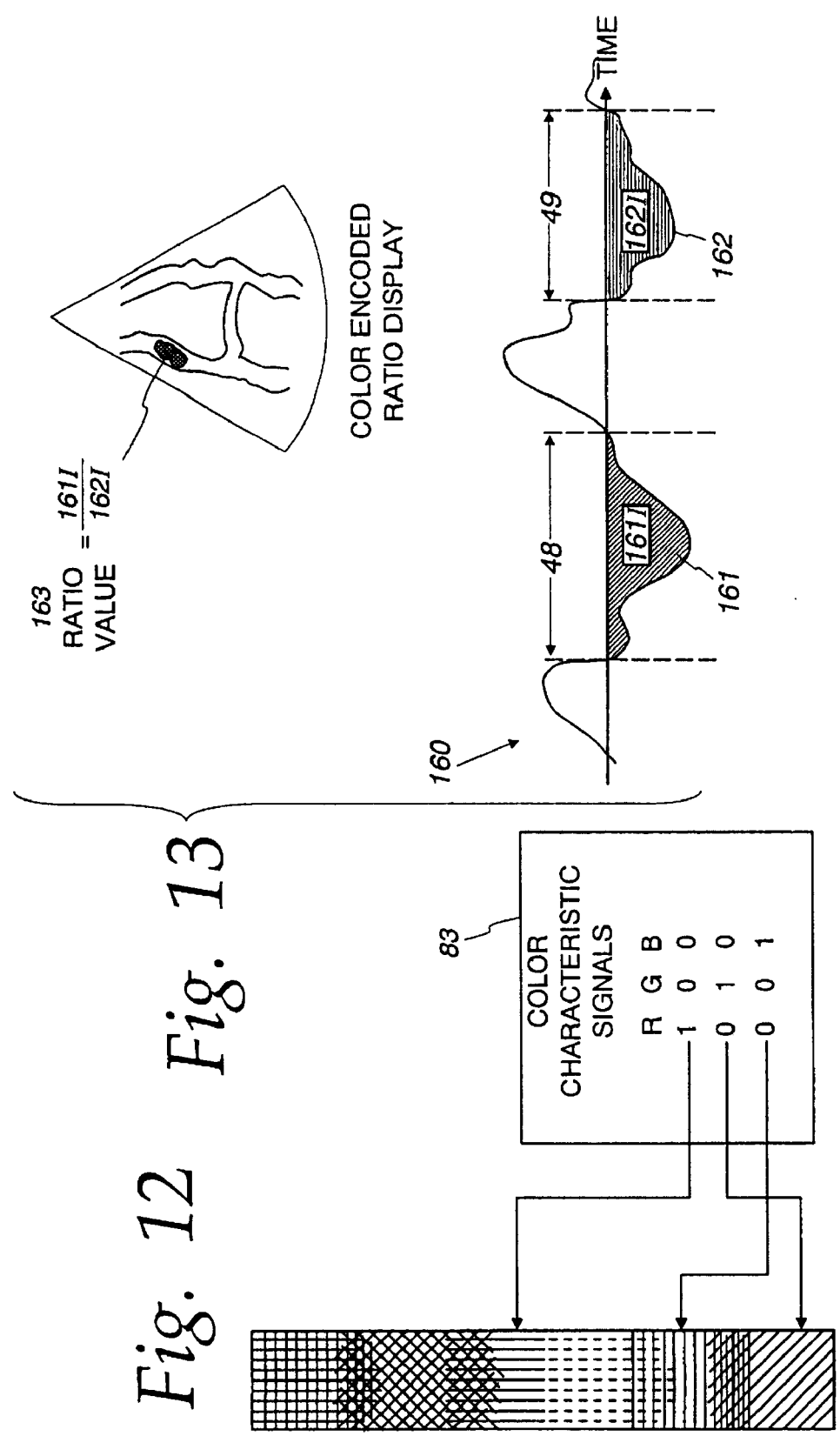

ULTRASOUND DISPLAY OF DISPLACEMENT

CROSS REFERENCE TO RELATED APPLICATIONS

The applicants claimed priority based on provisional application No. 60/297,572 filed Jun. 12, 2001 in the names of Bjorn Olstad, Steinar Bjaerum, and Kjell Kristoffersen.

BACKGROUND OF INVENTION

Certain embodiments of the present invention relate to an ultrasound machine for displaying an image of moving structure. More particularly, certain embodiments relate to displaying displacement of moving structure such as distance moved and deformation.

Echocardiography is a branch of the ultrasound field that is currently a mixture of subjective image assessment and extraction of key quantitative parameters. Evaluation of cardiac wall function has been hampered by a lack of well-established parameters that may be used to increase the accuracy and objectivity in the assessment of, for example, coronary artery diseases. Stress echo is such an example. It has been shown that the subjective part of wall motion scoring in stress echo is highly dependent on operator training and experience. It has also been shown that inter-observer variability between echo-centers is unacceptably high due to the subjective nature of the wall motion assessment.

Much technical and clinical research has focused on the problem and has aimed at defining and validating quantitative parameters. Encouraging clinical validation studies have been reported, which indicate a set of new potential parameters that may be used to increase objectivity and accuracy in the diagnosis of, for instance, coronary artery diseases. Many of the new parameters have been difficult or impossible to assess directly by visual inspection of the ultrasound images generated in real-time. The quantification has required a post-processing step with tedious, manual analysis to extract the necessary parameters.

Academic work has been done for validation of peak, mean systolic velocities as an indicator of, for example, ischemia in stress echo. A related parameter to peak systolic motion is displacement calculated as a velocity time integral during systole. Similar related displacement parameters may be defined for any sub-interval of the cardiac cycle. Displacement parameters derived from the time integral of velocity measurements or strain rate measurements have very low noise content compared to peak detection and are, therefore, attractive parameters to use for quantitative assessment of wall function. Therefore, it may be useful to design a mechanization that makes it easy to visually assess displacement of cardiac wall tissue in a quantitative manner.

Much of the prior art describes techniques for color mapping estimated imaging parameters such as tissue velocity and strain rate. A fixed mapping of a continuous range of color hues is typically used to indicate positive velocities or strain rates and a second fixed mapping of a continuous range of color hues is used to indicate negative velocities or strain rates. This type of color encoding makes it easy to identify reversals in velocities or strain rates. However, the tissue velocity imaging (TVI) and strain rate imaging (SRI) modes and associated color mapping schemes in the prior art are not, by themselves, well suited for visual determination of other parameters, such as displacement measured as time integrated velocities or time integrated strain rates over a portion of the cardiac cycle.

A need exists for an approach to more easily visualize tissue displacement information, such as time integrated velocity and time integrated strain rate, in a two-dimensional dimensional ultrasound image.

SUMMARY OF INVENTION

An embodiment of the present invention provides an ultrasound system for generating an image responsive to moving cardiac structure by displaying color characteristics representative of tissue displacement.

An apparatus is provided in an ultrasound machine for generating an image responsive to moving structure within a region of interest of a subject and displaying a color characteristic representing displacement of the moving structure. In such an environment apparatus displaying the color characteristic comprises a front-end arranged to transmit ultrasound waves into a structure and then to generate received signals in response to ultrasound waves backscattered from the structure in the region of interest over a time period. A processor is responsive to the received signals to generate a parameter value representing displacement of the moving structure during the time period and is responsive to the parameter value to generate a color characteristic signal representative of the displacement. A display is arranged to display a color representation of the displacement in response to the color characteristic signal.

A method embodiment is also provided in an ultrasound machine for generating an image responsive to moving structure within a region of interest of a subject and for displaying a color characteristic representing displacement of the moving structure. In such an environment, the method for displaying the color characteristic comprises transmitting ultrasound waves into the structure and generating received signals in response to ultrasound waves backscattered from the structure in the region of interest over a time period. A parameter value representing displacement of the moving structure during the time period is generated in response to the received signals. A color characteristic signal, representative of the displacement, is generated in response to the parameter value. A color representation of the moving structure is displayed in response to the color characteristic signal.

Certain embodiments of the present invention afford an approach to visualize the color display of the displacement of moving structure with a degree of convenience and accuracy previously unattainable in the prior art.

BRIEF DESCRIPTION OF DRAWINGS

FIG. 3 includes a cross-sectional view of a heart, a corresponding tissue velocity image (TVI) generated by the machine in FIG. 1, and a color legend generated by the machine in FIG. 1 that may be used to interpret the colors shown in the TVI image in accordance with an embodiment of the present invention.

FIG. 4 includes a cross-sectional view of a heart, a corresponding strain rate image (SRI) generated by the machine in FIG. 1, and a color legend generated by the machine in FIG. 1 that may be used to interpret the colors shown in the SRI image in accordance with an embodiment of the present invention.

FIG. 5 illustrates an exemplary ECG signal that may be generated by a timing event source and used by the machine in FIG. 1 to identify a time interval in accordance with an embodiment of the present invention.

FIG. 6 is a schematic cross-sectional view of the human heart including myocardium tissue bounded by a region of interest (ROI) that is designated by the machine shown in FIG. 1 under control of an operator in accordance with an embodiment of the present invention.

FIG. 12 is a graphic of a color characteristic legend and a signal diagram illustrating the color characteristic signals generated by the machine in FIG. 1 in terms of RGB values and how these values relate to the color characteristic legend in accordance with an embodiment of the present invention.

FIG. 13 is a graphic of a set of parameter signals and a ratio image generated from the set of parameter signals by the machine in FIG. 1 in accordance with an embodiment of the present invention.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

An embodiment of the present invention enables longitudinal tracking of moving structure and real time color visualization of displacement of the moving structure. As used herein, structure means non-liquid and non-gas matter, such as cardiac wall tissue. An embodiment of the present invention offers improved, real-time visualization and assessment of wall tissue function. The moving structure is characterized by a displacement parameter, which may be, for example, distance moved by the structure or deformation of the moving structure.

Figure 1:
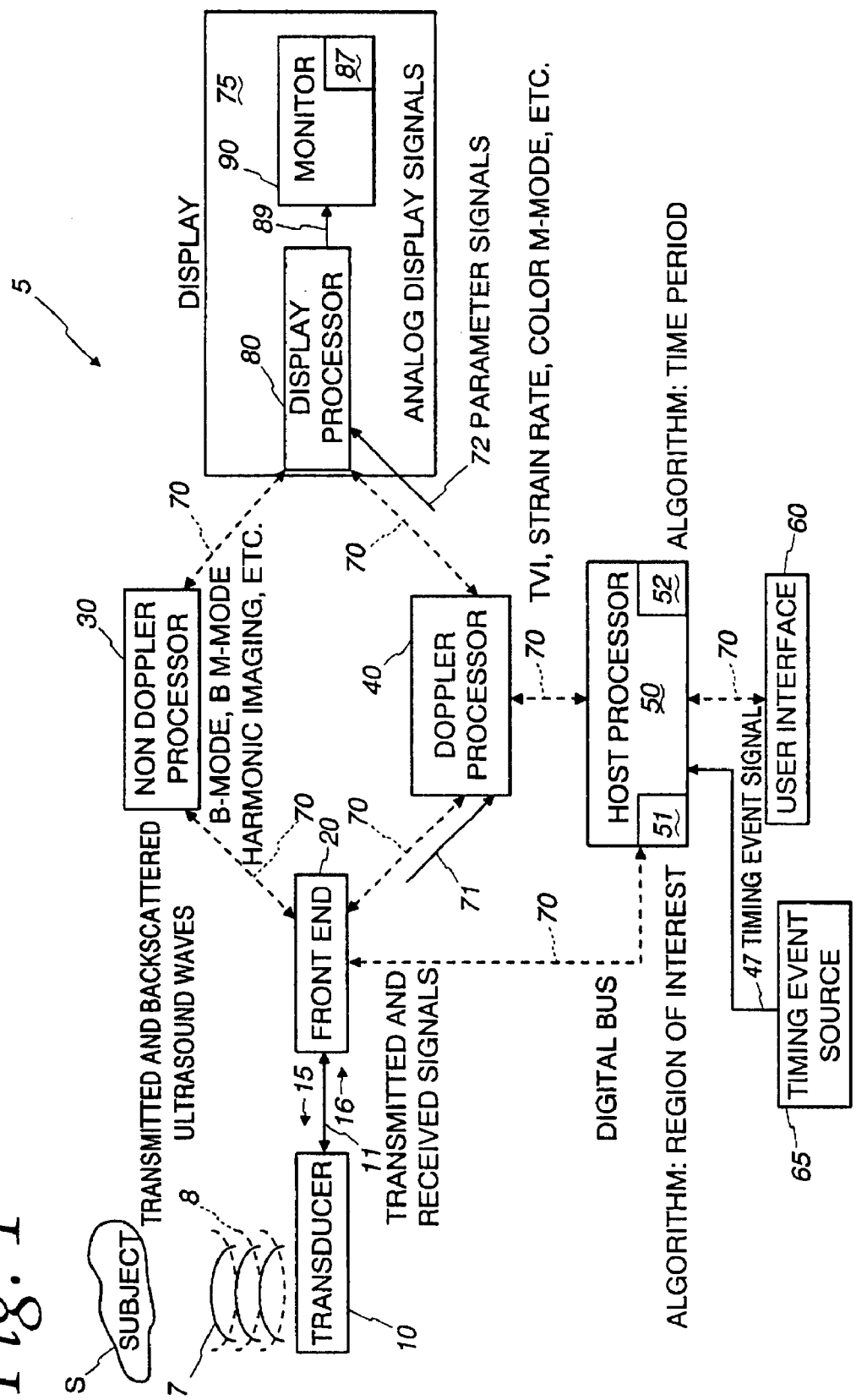
FIG. 1 is a schematic block diagram of an ultrasound machine made in accordance with an embodiment of the present invention.

FIG. 1 a schematic block diagram of an ultrasound machine 5 made in accordance with an embodiment of the present invention. A transducer 10 is used to transmit ultrasound waves 7 (solid curves in FIG. 1) into a subject S by converting electrical analog signals 15 to ultrasonic energy, and to receive ultrasound waves 8 (dashed curves in FIG. 1) backscattered from the subject S by converting ultrasonic energy to analog electrical signals 16.

A front-end 20 comprising a receiver, transmitter, and beamformer, is used to create the transmitted waveforms, beam patterns and receiver filtering techniques used for the various imaging modes. Front-end 20 performs the functions by converting digital data to analog data and vice versa. Front-end 20 interfaces at an analog interface 11 to transducer 10 and interfaces at a digital interface over a digital bus 70 to a non-Doppler processor 30 and a Doppler processor 40 and a host processor 50. Digital bus 70 may comprise several digital sub-buses, each sub-bus having its own unique configuration and providing digital data interfaces to various parts of the ultrasound machine 5.

Non-Doppler processor 30 comprises amplitude detection functions and data compression functions used for imaging modes such as B-mode, B M-mode, and harmonic imaging. Doppler processor 40 comprises clutter filtering functions and movement parameter estimation functions used for imaging modes such as tissue velocity imaging (TVI), strain rate imaging (SRI), and color M-mode. The two processors, 30 and 40, accept digital data from the front-end 20, process the data into sets of signal values 41, and pass the values to processor 50 and/or a display 75 over digital bus 70. The estimated values may be created using the received signals in frequency bands centered at the fundamental, harmonics, or sub-harmonics of the transmitted signals in a manner known to those skilled in the art.

Display 75 comprises scan-conversion functions, color mapping functions, and tissue/flow arbitration functions, performed by a display processor 80 which accepts digital parameter signals 72 from processors 30, 40, and 50, processes, maps, and formats the digital data for display, converts the digital display data to analog display signals 89, and passes the analog display signals 89 to a monitor 90.

Monitor 90 accepts the analog display signals 89 from display processor 80 and displays the resultant image 87 to the operator on monitor 90.

A user interface 60 allows user commands to be input by the operator to the ultrasound machine 5. User interface 60 comprises a keyboard, mouse, switches, knobs, buttons, track ball, and on screen menus (not shown).

Host processor 50 is the main, central processor of the ultrasound machine 5 and interfaces to various other parts of the ultrasound machine 5 through digital bus 70. Host processor 50 executes the various data algorithms and functions for the various imaging modes. Digital data and commands may be transmitted and received between the host processor 50 and other various parts of the ultrasound machine 5. The functions performed by processor 50 may be performed by multiple processors or may be integrated into processors 30, 40, or 80, or any combination thereof.

Figure 2:
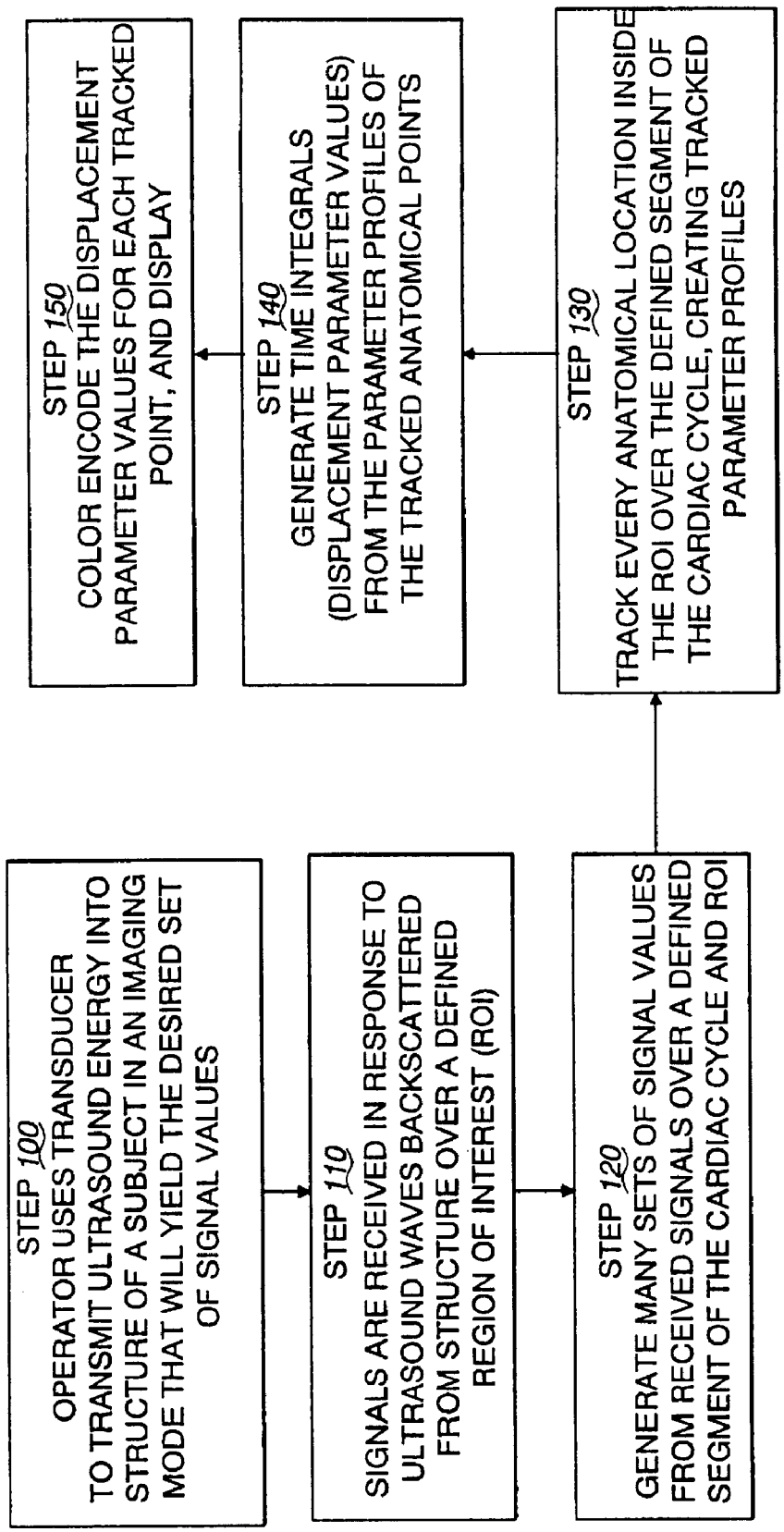
FIG. 2 is a flowchart of a method performed, at least in part, by the machine shown in FIG. 1 in accordance with an embodiment of the present invention.
Figure 7:
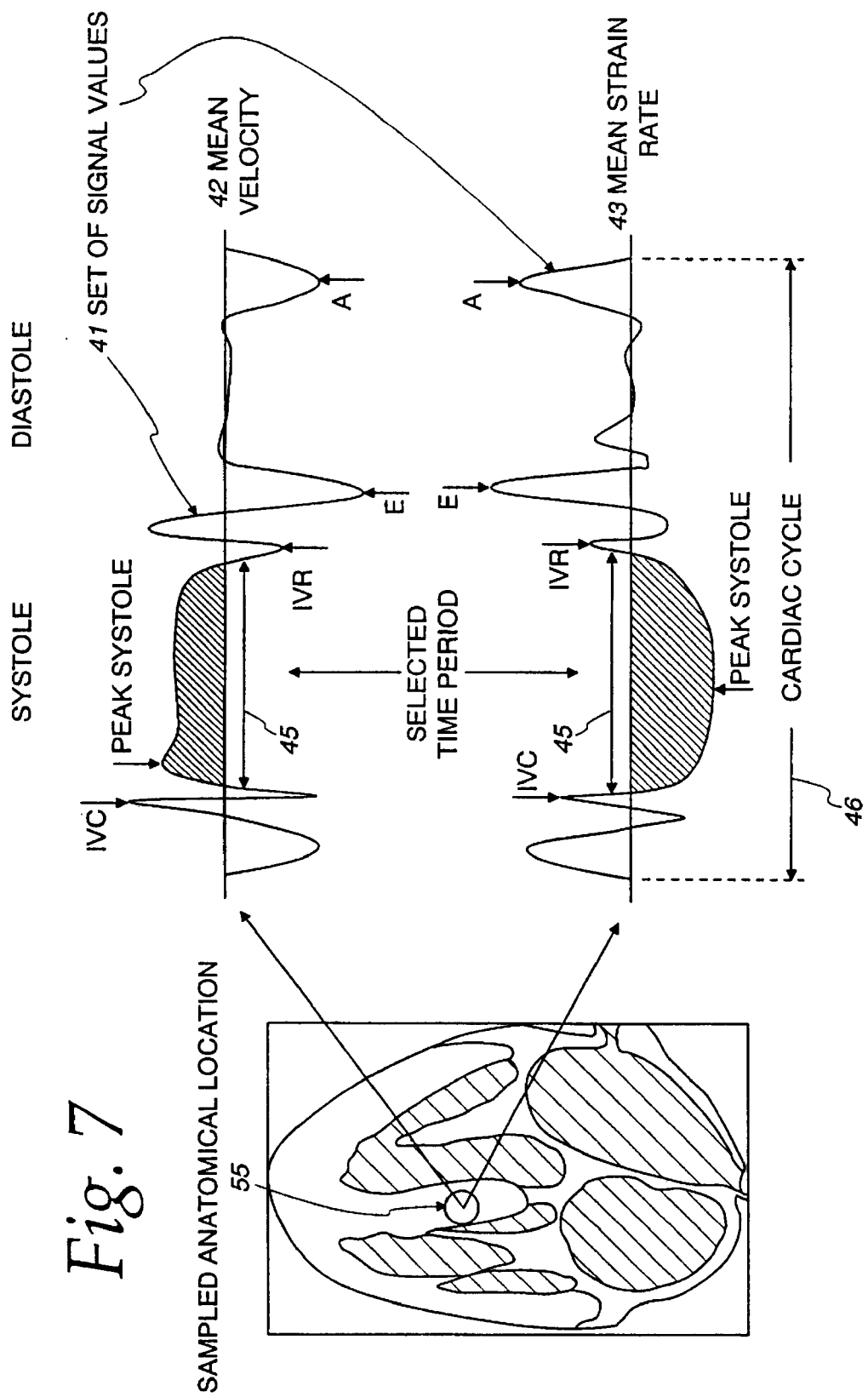
FIG. 7 is a schematic cross-sectional view of the heart shown in FIG. 6 also graphically representing mean velocity and mean strain rate profiles as a function of time, measured longitudinally in an apical view for a sampled anatomical location in accordance with an embodiment of the present invention.

Referring to FIG. 2, in step 100 an operator uses transducer 10 to transmit ultrasound energy into the appropriate anatomical structure, such as cardiac tissue 105 (see FIG. 3), of the subject in an imaging mode (such as TVI or SRI) that yields a desired set of signal values 41 (see FIG. 7) of the anatomical structure 105. As shown in FIG. 7, the set of signal values 41 typically comprises longitudinal estimates of mean tissue velocity 42 or mean tissue strain rate 43 parameters. The specification herein uses the examples of tissue velocity imaging (TVI) and tissue strain rate imaging (SRI). Based on the specification herein, those skilled in the art may also provide an embodiment that employs other estimated parameters that form a set of signal values.

Referring to FIG. 3, in TVI mode a fixed, continuous range of color hues is used to indicate positive velocities and a second fixed, continuous range of color hues is used to indicate negative velocities. Typically, red/yellow hues show anatomical motion towards the transducer 10 and blue/green hues show motion away from the transducer 10. The color hues 84 are illustrated in the color characteristic legend 85 shown in FIG. 3. The various cross-hatchings and lines in the color characteristic legend 85 of FIG. 3 represent a continuous range of color hues. Going from the top of the color characteristic legend 85 to the bottom, the color hues transition from yellow to orange to red representing the positive velocity segment 81 of the color characteristic legend 85 and then violet to blue to green, representing the negative velocity segment 82 of the color characteristic legend 85. However, the color hues 84 that make up the color characteristic legend 85 may be any continuous, semi-continuous, or discrete range of color hues that provide good discrimination between levels of the set of signal values 41. The portions of the color characteristic legend 85 in which cross-hatched lines intersect represent a blending of color hues. Similarly, FIG. 4 illustrates a color representation of strain rate imaging.

In step 110 of FIG. 2, ultrasound energy is received into transducer 10 and signals are received into front-end 20 in response to ultrasound waves 8 backscattered from the structure 105 over an operator-defined region of interest (ROI) 86 (see FIG. 6). The operator brings up a scaleable ROI 86 on monitor 90 through the user interface 60 to select a spatial or anatomical region to process such as the septum 104 of the heart (see FIG. 6). The ROI may be chosen to cover the entire displayed image 87 if desired. Such a selection of an ROI 86 forces the subsequent processing to segment, track, and time integrate a set of signal values 41 and display the resultant time integrated values in an image 87 for that specific region. The approach may, for example, be useful if the operator wants to provoke a good visualization of time integrated myocardial velocities in a specific region. In other similar embodiments, the ROI 86 may be selected automatically or as a combination of manual and automatic methods. For example, an algorithm 51 (see FIG. 1) for automatic identification of an ROI 86 may be designed and embedded in the host processor 50 to separate the myocardium from cavities. Well-known segmentation and thresholding techniques operating on the data of the set of signal values 41 may be used. The ROI 86 is automatically sized and positioned on display image 87 based on the results of the techniques.

Figure 8:
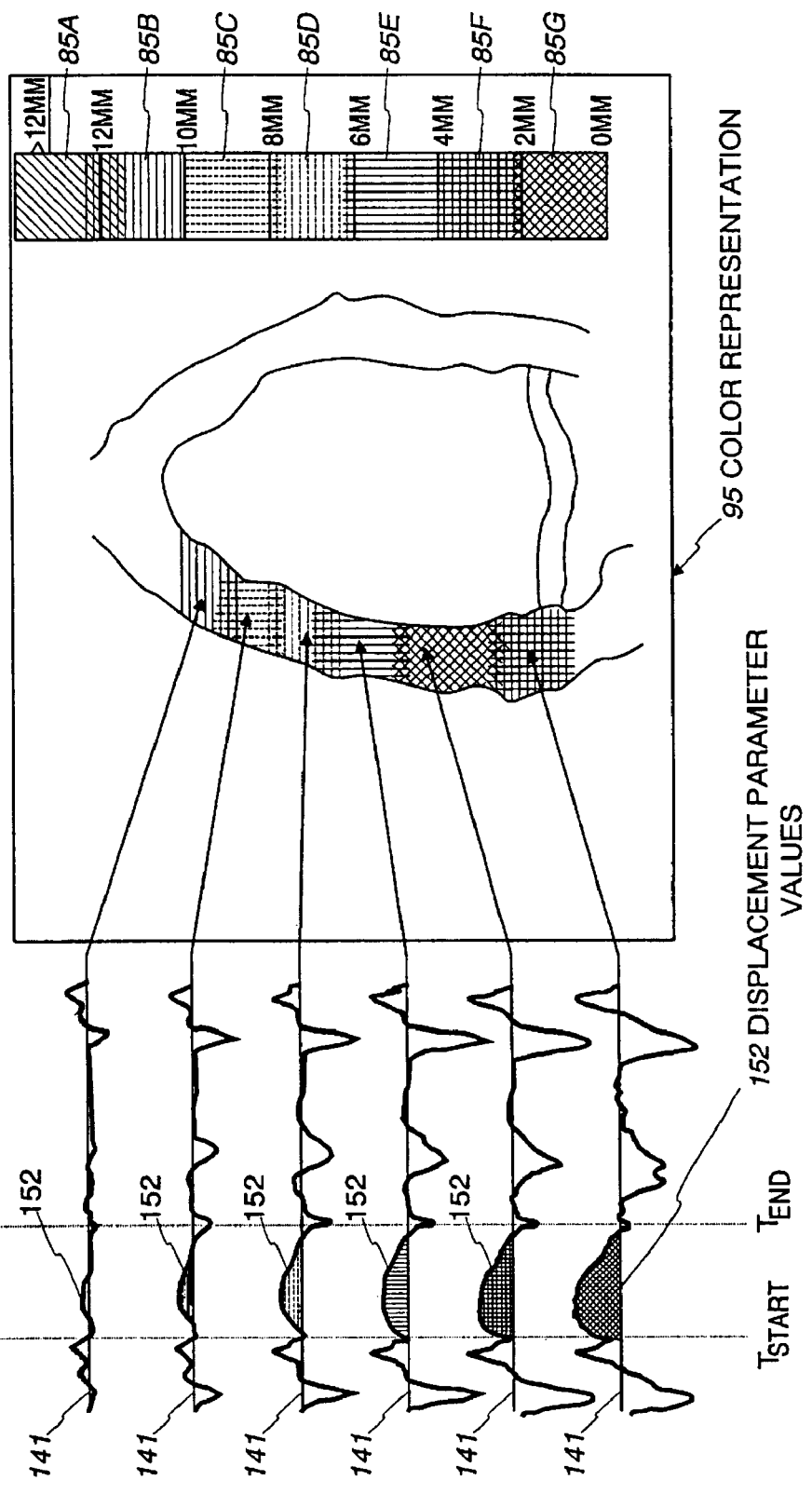
FIG. 8 is a graph illustrating time integrated velocity profiles and color encoding generated by the method shown in FIG. 2, together with an exemplary display of cardiac tissue using the color encoding in accordance with an embodiment of the present invention.

In step 120 of FIG. 2, received signals 71 are sent from front-end 20 to Doppler processor 40 over digital bus 70. Many sets of signal values 41, such as mean velocity 42 or mean strain rate 43, are generated from the received signals 71 over a segmented time period 45 and ROI 86 by Doppler processor 40. The operator selects, through the user interface 60, a desired time interval 45 to process, such as systole, which is a sub-interval of the cardiac cycle 46 (see FIG. 7). In FIG. 8, the time interval is designated by $T_{start}$ and $T_{end}$. The time interval is determined from a timing signal 47 generated from a timing event source 65 (FIG. 1) and/or from characteristic signatures in the set of signal values 41. An example of such a timing signal 47 is an ECG signal (see FIG. 5). Those skilled in ultrasound also know how to derive timing events from signals of other sources such as a phonocardiogram signal, a pressure wave signal, a pulse wave signal, or a respiratory signal. Ultrasound modalities such as spectrum Doppler or M-modes may also be used to obtain timing information.

$T_{start}$ is typically selected by the operator as an offset from the R-event in the ECG signal. $T_{end}$ is set such that the time interval covers a selected portion of the cardiac cycle such as systole. It is also possible to select a time period 45 corresponding to the complete cardiac cycle 46. Another possibility is to limit the time period 45 to the systolic time period in order to display a color representation that is optimized for visualization of time integrated systolic parameters. Other sub-intervals of the cardiac cycle 46 may also be applied.

FIG. 7 graphically illustrates typical sets of signal values 41 for velocity 42 and strain rate 43 which may be segmented into desired time periods based on signature characteristics of the sets. For reference, the profiles in FIG. 7 are annotated with the times corresponding to: IVC=isovolumetric contraction, IVR=isovolumetric relaxation, E=early diastolic velocity, and A=late diastolic velocity. Caution must be taken in the selection of the time interval such that, for example, motion in the IVC or IVR period may be excluded from the analysis, if desired. An automatic function may be implemented to recognize and exclude the unwanted events from the time interval.

In other possible embodiments, the time interval may be selected automatically or as a combination of manual and automatic methods. For example, the time period 45 may be determined automatically with an algorithm 52 (see FIG. 1) embedded in host processor 50. The algorithm 52 may use well-known techniques of analyzing the sets of signal values 41, as shown in FIG. 7, looking for key signal signature characteristics and defining a time period 45 based on the characteristics, or similarly, analyzing the ECG signal 47.

Figure 10:
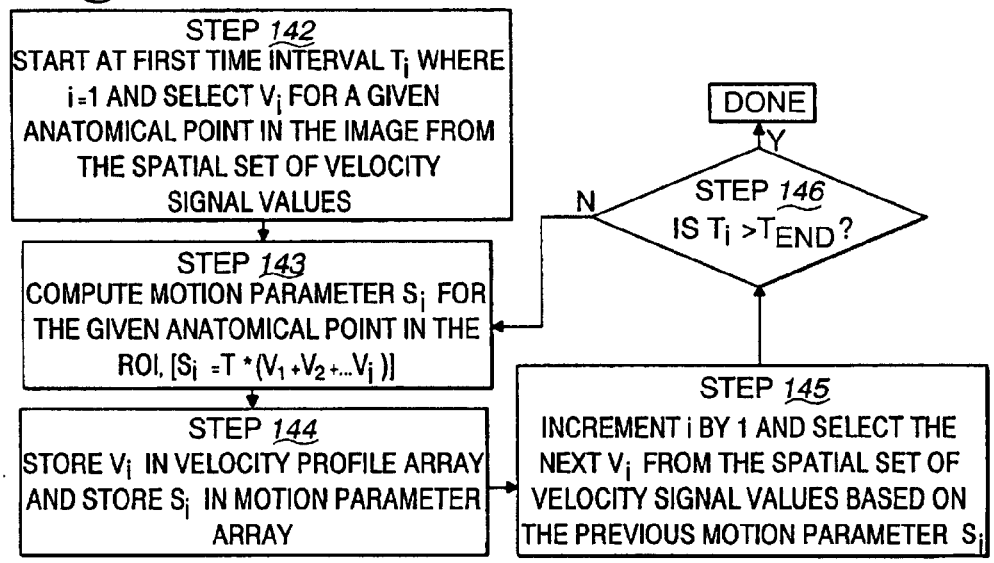
FIG. 10 is a flowchart of the longitudinal tracking function that generates the graphs shown in FIG. 9 and is executed by the machine shown in FIG. 1 in accordance with an embodiment of the present invention.

In step 130 of FIG. 2, the operator initiates, through user interface 60, real time tracking of every sampled anatomical location 55 (FIG. 7) inside the selected ROI 86 over the selected time period 45 of the cardiac cycle 46. The spatial set of signal values 41 are sent from Doppler processor 40 to host processor 50, where a tracking function 147 is applied to the set of signal values 41. FIG. 10 is a flow chart of the tracking function 147.

As an introduction to the tracking function 147, a tracked velocity parameter profile 141 ($V_1, V_2, \ldots, V_n$) (FIG. 9) for a given sampled anatomical location 55 in the myocardium 105, is created over the time period $T_{start}$ to $T_{end}$ by converting the spatial set of velocity values 42 into a motion parameter profile 151 in time using host processor 50 by computing the series of time integrals ($S_1, S_2, \ldots, S_n$) where:

$$S_i = T*(V_1 + V_2 + \ldots + V_i) \qquad \text{[Equation 1]}$$

and where T is the time delay between two consecutive velocity measurements (T is typically based on the frame rate of the imaging mode). $S_i$ (motion value) is then the longitudinal distance in mm (from reference time $T_{start}$ location) that a sample of tissue in the myocardium has moved at time segment $T_i$, thus allowing the isolated tissue sample to be tracked longitudinally (along the ultrasound beam) over the time interval $T_{start}$ to $T_{end}$ by host processor 50. The tracking function estimates the new anatomical location of the tracked sample tissue after every time segment $T_i$ and determines tracked velocities (or other estimated parameters) at the new anatomical locations. The tracking is done for each sampled anatomical location 55 in the selected ROI 86.

Figure 9:
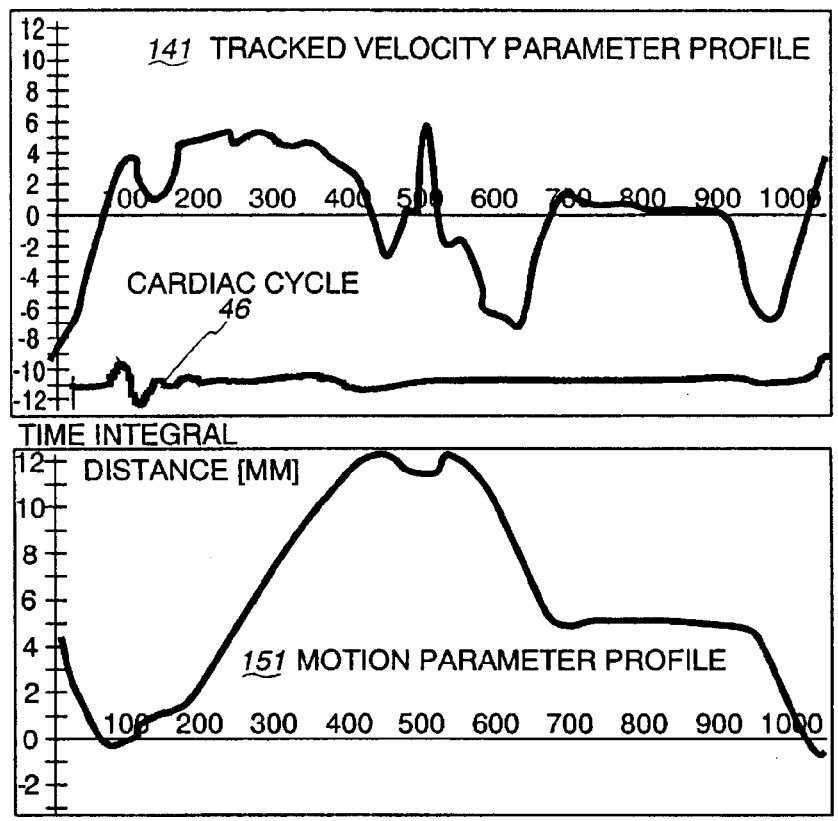
FIG. 9 shows graphs of a tracked velocity parameter profile and a motion parameter profile generated by the tracking algorithm flowcharted in FIG. 10 in accordance with an embodiment of the present invention.

The upper part of FIG. 9 shows a resultant tracked velocity parameter profile 141 of a sampled anatomical location 55 in the image as a function of time for a complete cardiac cycle 46. The lower part of FIG. 9 shows the corresponding resultant longitudinal motion parameter profile 151 (integrated velocity profile, $S_1, S_2, \ldots, S_n$) of the same sampled anatomical location in the image. Motion along the ultrasound beam may be accurately tracked with the technique allowing the appropriate velocity parameter profiles (or other estimated parameter profiles) to be generated for the corresponding anatomical locations. The tracked estimated parameter profile 141 for each anatomical location is stored in the memory of host processor 50 as a sampled array of estimated parameter values. As a result, the stored parameter profile history corresponds to each anatomical location, instead of just a spatial location in the image.

Two-dimensional velocity estimation is necessary for accurate tracking when a substantial part of the motion of the structure is orthogonal to the beam. Other tracking techniques may be employed as well.

As an alternative to tracking, spatial estimated parameter profiles may be constructed by the host processor 50 from the set of signal values and correlated to fixed spatial locations in the image instead of to anatomical locations. Subsequent time integration will then be performed at fixed spatial locations over the time period 45.

The specific steps of the preferred tracking function 147 are now described for a given sampled anatomical location 55 in the ROI 86. A spatial set of mean velocity values 42 is estimated in step 120 of FIG. 2 so that the motion values $S_i$ may be calculated for tracking. The mean velocity values are generated by Doppler processor 40 in a well-known manner.

Referring to FIG. 10, in step 142 of tracking function 147, processor 50 selects $V_i$ for a given anatomical location in the image from a spatial set of velocity values 42 in the ROI 86 corresponding to time interval $T_i$ where i=1 ($T_1$ is $T_{start}$).

In step 143 of tracking function 147, processor 50 computes the motion value $S_i$ for the given anatomical location in the ROI, as $$S_i = T^*(V_1 + V_2 + \ldots + V_i)$$ [Equation 1]

(Note that for i=1, $S_1 = T^*V_1$)

In step 144 of tracking function 147, processor 50 stores $V_i$ in tracked velocity parameter profile array 141 and $S_i$ is stored in motion parameter profile array 151 along with the current spatial position of the anatomical location. Other estimated parameters, such as strain rate, corresponding to the tracked anatomical location may be stored in respective tracked profile arrays as well.

In step 145 of tracking function 147, i is incremented by one (corresponding to the next sample time, T seconds later) and the next $V_i$ is selected from the spatial set of velocity values 42 based on the motion parameter $S_i$ previously computed and the previous spatial position of the anatomical location ($S_i$ represents the longitudinal spatial movement in mm of the anatomical location over time interval $T_i = i^*T$).

In step 146 of tracking function 147, the function checks to see if $T_{end}$ has been exceeded. If $T_{end}$ has not been exceeded, the function proceeds back to step 143 and computes the next motion parameter value $S_i$ in the series using Equation 1. The iterative process is followed until the full arrays of tracked velocity parameter profiles 141, motion parameter profiles 151, and any other desired estimated parameter profile have been created and stored over the complete time interval $T_{start}$ to $T_{end}$.

The tracking function 147 is performed simultaneously for each anatomical location in the ROI 86.

Figure 11:
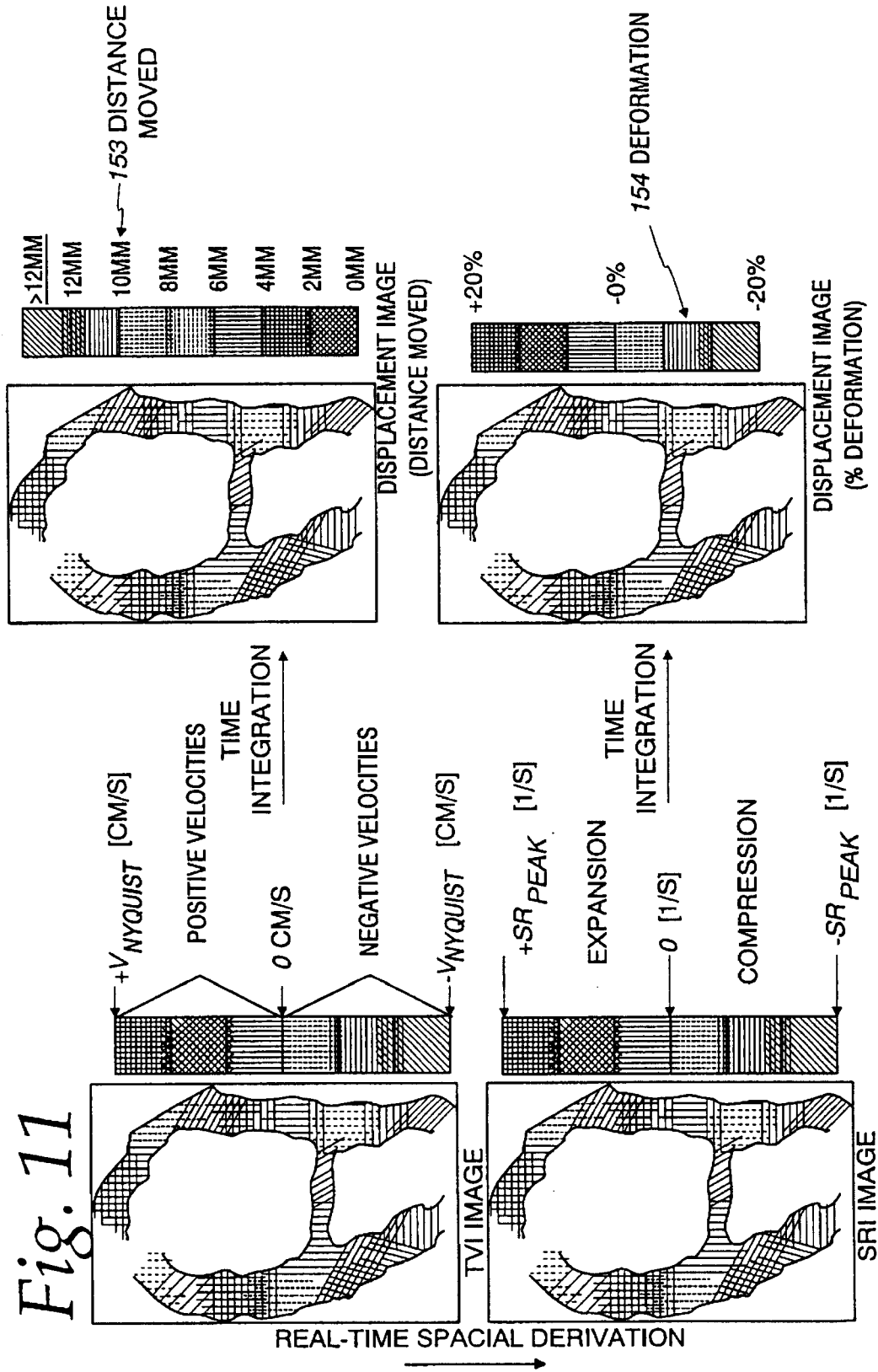
FIG. 11 shows displays of tissue structure displacement generated by the machine in FIG. 1 illustrating the relationship between TVI and SRI and the time integration of velocity and strain rate which is performed by the method shown in FIG. 2 in accordance with an embodiment of the present invention.

FIG. 11 illustrates the function of generating the displays of time integrated displacement parameters for the imaging modes of TVI and SRI. When velocity estimates are integrated over time, the resultant displacement parameter value 152 (shaded areas of FIG. 8) is a distance moved 153 (FIG. 11) in units of length such as millimeters (mm). A resultant display of time integrated velocity is shown in the upper right of FIG. 11. The display represents displacement of the cardiac tissue over the integrated time period.

Strain rate SR, in units of 1/seconds, is computed as radial gradients of the velocity estimates. Strain rate SR is a spatial derivation of velocity and is the rate at which tissue velocity is changing over a radial distance. When the gradient of the tissue velocity is computed along the ultrasound beam, a strain rate image will be obtained as shown in the lower left of FIG. 11. The computation may be expressed as:

$$SR = \Delta V / \Delta x$$ [Equation 2]

where SR is strain rate and $\Delta V$ is the change in velocity over the longitudinal distance $\Delta x$ (longitudinal tissue segment). SR is typically color encoded at $\Delta x/2$, the center of the tissue segment.

When strain rate is integrated over time, the resultant displacement parameter value 152 is a deformation 154 (FIG. 11) that is unitless but may be expressed as a total deformation of the tissue in percentage as shown in the lower right of FIG. 11 resulting in a measure of the deformation 154 of a segment of tissue around $\Delta x/2$ which is the center of the tissue segment $\Delta x$. If the time integration is performed from $T_{start}$ to $T_{end}$, the value of the time integral 152 is a measure of the relative deformation 154 of the tissue segment over the time interval. If the time integration starts at, for example, the beginning of systole (contraction phase of the heart cycle), and the value is calculated to be 0.5 at the end of systole, then the tissue segment $\Delta x$ surrounding the location $\Delta x/2$ has a deformation of 50%. The deformation 154 is used to color encode the location $\Delta x/2$ and is calculated based on samples in a neighborhood around the location continuous, $\Delta x/2$ for a given tissue segment $\Delta x$.

In step 140 of FIG. 2, the stored, tracked estimated parameter profiles 141 (e.g. longitudinal mean velocity or strain rate profiles) for each sampled anatomical location 55 are integrated over the time interval $T_{start}$ to $T_{end}$ by the host processor 50 by a time integration function in host processor 50 which approximates the true time integral by summing tracked values as follows:

$$S_{int} = T^*(Q_{start} + Q2 + Q3 + \ldots + Q_{end})$$ [Equation 3]

is the time integrated value 152 (displacement parameter value), $Q_{start}$ is the first value in the tracked movement parameter profile 141 (corresponding to $T_{start}$) and $Q_{end}$ is the last (corresponding to $T_{end}$) For tissue velocity imaging, Q is V and for tissue strain rate imaging, Q is SR. Each shaded area 152 under the profiles in FIG. 8 represent a displacement parameter value calculated by integrating velocity values 42 over the time interval $T_{start}$ to $T_{end}$.

The time integration function is performed simultaneously for each anatomical location in the ROI 86.

Care should be taken by the operator to adjust the Nyquist frequency of the imaging mode such that aliasing does not occur. With aliasing present in the data, erroneous results occur. Alternatively, well known automatic aliasing correction techniques may be employed.

In step 150 of FIG. 2, the time integrated displacement parameter value $S_{int}$ for each tracked anatomical location is used to color encode the associated location in the image in display processor 80. The displacement parameter values 152 are sent from host processor 50 to display processor 80 for image formatting and color encoding. The time integrated values $S_{int}$ may either be color encoded with the same color encoding (color mapping table) as the underlying TVI or SRI imaging mode, or a dedicated color encoding may be devised for the time integrated display. Clinical work on time integrated velocities shows that it is advantageous to design a color encoding such that quantitative values may be inferred directly from the color encoding.

FIG. 8 illustrates a display of color-encoded time integrated velocities (i.e. displacement parameter values) of a myocardial segment of the heart in a displayed color representation 95 on monitor 90 (FIG. 1) using a pre-defined, discrete color mapping table where N discrete colors are used to visualize the time integrated velocities. In the example, seven discrete color hues are used to separate between time integrated velocities: 0–2 mm, 2–4 mm, 4–6 mm and to >12 mm in color legend areas 85A–85G respectively (see color legend of FIG. 8). The number of discrete colors may be increased over the scale of the color legend in order to get a finer separation of time integrated values. The color hues are typically represented in memory as red, green, blue (RGB) values as shown in FIG. 12. The RGB values constitute the color characteristic signals 83. The RGB values may be represented as normalized values between 0 and 1, as shown in FIG. 12. Therefore, to represent a perfectly red hue, the RGB values are (1 0 0). For a perfectly green hue, the RGB values are (0 1 0), and for blue (0 0 1). An RGB combination of (1 1 1) yields a perfectly white hue and an RGB combination of (0 0 0) yields a perfectly black hue. Any other color hue may be represented by various combinations of RGB values. For example, if an RGB value is (0.5 0.8 0.3), a combination of unequal parts of red, green, and blue hues each with a different weighting, the result is some new color hue.

As an alternative, time integration may be performed after each new tracked element in the tracked movement parameter profile array is added or after each new spatial element is added to the spatial movement parameter profile, instead of waiting until $T_{end}$ to perform the integration allowing a constant update of the displayed time integrated values within the time interval $T_{start}$ to $T_{end}$.

The time integrated value corresponding to the cutoff for the color encoding of the highest time integration value may be preset in order to relate the time integration values to normal physiological values. Typically, a normal physiological value may be used for the preset. The setting will depend on the image view and the stress level in a stress echo exam. If for instance the normal basal peak velocity integral is selected, one can determine whether a patient has normal longitudinal function at the given stress level simply by checking whether the color corresponding to the highest velocity integral index appears in the basal segment. Different anatomical segments may be addressed in a similar manner. A reduction in longitudinal function may be quantified by evaluating the percentage of the normal velocity integral range that is actually observed. The assessment may also indirectly be an assessment of global function because of the strong correlation between Ejection Fraction and systolic, longitudinal motion of the mitral annulus.

As another possible embodiment, more than one displacement parameter value 152 may be extracted from the same cardiac cycle and combined for display. An example is the computation and display of ratio images where the process described herein for determination of time integrated values is performed over two time periods and the ratio between the two time integrated values is used to color encode the spatial or tracked anatomical locations.

Referring to FIG. 13, the displacement parameter value is a ratio value 163. The ratio value 163 is derived from a set of displacement parameter signals 160 comprising a first parameter signal 161 representing a first displacement 1611 of the moving structure 105 over a first time period 48 and a second parameter signal 162 representing a second displacement 1621 of the moving structure 105 over a second time period 49. The ratio value 163 is the ratio of the time integrated value 1611 (first displacement) of the first parameter signal 161 and the time integrated value 1621 (second displacement) of the second parameter signal 162. The ratio value 163 is then color encoded and displayed for each sampled anatomical location 55 in the ROI 86. For example, the first time period may correspond to systole and the second time period may correspond to IVR allowing quantification and displaying of IVR activity relative to systolic excursions.

Images of ratio values remove the angle dependence of, for example, tissue velocity imaging because the unknown cosine modulation caused by the angle of incidence is the same in both measurements. Ratios of other combinations may be calculated and displayed as well. For example, it may be useful to compute ratios between time integrated values and peak signal values for a given time period. The ratio contains information related to acceleration in the selected time period.

The embodied method may be applied to any imaging mode of the ultrasound machine 5 for moving structure, for any estimated parameter (e.g. velocity, strain rate, power, amplitude, etc.).

In summary, certain embodiments of the present invention afford an approach to more easily visualize tissue displacement parameter information, such as time integrated velocity and time integrated strain rate, in a two-dimensional ultrasound image.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments failing within the scope of the appended claims.

What is claimed is:

1. In an ultrasound machine for generating an image responsive to moving structure within a region of interest of a subject, apparatus for displaying a color characteristic representing displacement of the moving structure comprising:

a front-end arranged to transmit ultrasound waves into the structure and to generate received signals in response to ultrasound waves backscattered from the structure in the region of interest over a time period;

a processor responsive to the received signals to generate a parameter value representing displacement of the moving structure during the time period and responsive to the parameter value to generate a color characteristic signal representative of the displacement; and a display arranged to display a color characteristic representative of the displacement of the moving structure in response to the color characteristic signal.

2. The apparatus of claim 1 wherein the moving structure comprises cardiac tissue.

3. The apparatus of claim 1 wherein the displacement represents one of distance moved by the moving structure and deformation of the moving structure.

4. The apparatus of claim 1 wherein the color characteristic comprises hue.

5. The apparatus of claim 1 wherein the processor generates the parameter value by summing a set of signal values representing velocities of the moving structure over the time period.

6. The apparatus of claim 1 wherein the processor generates the parameter value by summing a set of signal values representing strain rates of the moving structure over the time period.

7. The apparatus of claim 1 wherein the time period comprises at least a portion of a cardiac cycle selectable by a user of the machine including at least one of systole, diastole, IVC, IVR, E-wave, and A-wave.

8. The apparatus of claim 7 wherein the portion of the cardiac cycle is selectable from at least one of the set of signal values and a timing event signal comprising at least one of an ECG signal, a phonocardiogram signal, a pressure wave signal, a pulse wave signal, and a respiratory signal.

9. The apparatus of claim 1 wherein the parameter value represents displacement of a sampled anatomical location of the moving structure within the region of interest.

10. The apparatus of claim 1 wherein the parameter value is derived from a set of parameter signals, wherein the set of parameter signals comprises a first parameter signal representing a first displacement of the moving structure and a second parameter signal representing a second displacement of the moving structure, and wherein the color characteristic signal represents the ratio of the first displacement and the second displacement.

11. In an ultrasound machine for generating an image responsive to moving structure within a region of interest of a subject, a method of displaying a color characteristic representing displacement of the moving structure comprising:

transmitting ultrasound waves into the structure;

generating received signals in response to ultrasound waves backscattered from the structure in the region of interest over a time period;

generating a parameter value representing displacement of the moving structure during the time period in response to the received signals;

generating a color characteristic signal representative of the displacement in response to the parameter value; and displaying a color characteristic representative of the displacement of the moving structure in response to the color characteristic signal.

12. The method claim 11 wherein the moving structure comprises cardiac tissue.

13. The method of claim 11 wherein the displacement represents one of distance moved by the moving structure and deformation of the moving structure.

14. The method of claim 11 wherein the color characteristic comprises hue.

15. The method of claim 11 wherein said generating a parameter value comprises summing a set of signal values representing velocities of the moving structure over the time period.

16. The method of claim 11 wherein said generating a parameter value comprises summing a set of signal values representing strain rates of the moving structure over the time period.

17. The method of claim 11 wherein the time period comprises at least a portion of a cardiac cycle selectable by a user of the machine.

18. The method of claim 17 wherein the portion of the cardiac cycle is selectable from at least one of the set of signal values and a timing event signal comprising at least one of an ECG signal, a phonocardiogram signal, a pressure wave signal, a pulse wave signal, and a respiratory signal.

19. The method of claim 11 wherein the parameter value represents displacement of a sampled anatomical location of the moving structure within the region of interest.

20. The method of claim 11 wherein the parameter value is derived from a set of parameter signals, wherein the set of parameter signals comprises a first parameter signal representing a first displacement of the moving structure and a second parameter signal representing a second displacement of the moving structure, and wherein the color characteristic signal represents the ratio of the first displacement and the second displacement.

* * * * *